(12) United States Patent
Krah, III

(10) Patent No.: US 7,572,445 B2
(45) Date of Patent: Aug. 11, 2009

(54) PEPTIDES FOR DETECTION OF ANTIBODY TO PORCINE REPRODUCTIVE RESPIRATORY SYNDROME VIRUS

(75) Inventor: Eugene Regis Krah, III, Freeport, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 280 days.

(21) Appl. No.: 11/362,599

(22) Filed: Feb. 24, 2006

(65) Prior Publication Data

US 2006/0234211 A1 Oct. 19, 2006

Related U.S. Application Data

(60) Provisional application No. 60/656,348, filed on Feb. 25, 2005.

(51) Int. Cl.
*A61K 39/00* (2006.01)
*A61K 39/42* (2006.01)
*A61K 5/55* (2006.01)
*G01N 33/53* (2006.01)
*C12P 21/04* (2006.01)
*C12P 21/06* (2006.01)

(52) U.S. Cl. .............. 424/134.1; 424/9.34; 424/133.1; 424/139.1; 424/147.1; 435/7.1; 435/69.1; 435/69.7

(58) Field of Classification Search ........................ None
See application file for complete search history.

(56) References Cited

U.S. PATENT DOCUMENTS 5,620,691 A 4/1997 Wensvoort et al.
5,998,601 A 12/1999 Murtaugh et al.
2004/0247617 A1 12/2004 Liao et al.
2007/0003570 A1 1/2007 Murtaugh et al.

FOREIGN PATENT DOCUMENTS

| EP | 0 952 219 | 10/1999 |
| WO | WO 96/04010 | * 2/1996 |
| WO | WO 98/50426 | * 11/1998 |
| WO | WO 02/095040 | 11/2002 |

OTHER PUBLICATIONS

U.S. Appl. No. 60/656,348, filed Feb. 25, 2005.
Stanley, et al., "Construction of a new family of high efficiency bacterial expression vectors: identification of cDNA clones coding for human liver proteins", The EMBO Journal, vol. 3, No. 6, p. 1429-1434 (1984).
International Search Report and Written Opinion for corresponding PCT application PCT/US2006/006612 dated Aug. 22, 2006.
Witte, et al., "Development of a Recombinant Nucleoprotein-Based Enzyme-Linked Immunosorbent Assay for Quantification of Antibodies against Porcine Reproductive and Respiratory Syndrome Virus", Clinical and Diagnostic Laboratory Immunology, vol. 7, No. 4, (2000) p. 700-702.
Wootton, et al., "Antigenic Structure of the Nucleocapsid Protein of Porcine Reproductive and Respiratory Syndrome Virus", Clinical and Diagnostic laboratory Immunology, vol. 5, No. 6, (1998) p. 773-779.
Polson, et al., "A filed-based performance comparison of the new IDEXX HerdChek PRRS 2XR ELISA with the original HerdChek PRRS ELISA", American Association of Swine Veterinarians, (2003) p. 2637-272.

* cited by examiner

*Primary Examiner*—Bruce Campell
*Assistant Examiner*—Sharon Hurt
(74) *Attorney, Agent, or Firm*—McDonnell Boehnen Hulbert & Berghoff LLP

(57) ABSTRACT

The invention provides compositions and methods for the detection and quantification of PRRSV antibodies and antibody fragments using polypeptides.

22 Claims, No Drawings

SEQUENCE LISTING

```
<160> NUMBER OF SEQ ID NOS: 18

<210> SEQ ID NO 1
<211> LENGTH: 102
<212> TYPE: PRT
<213> ORGANISM: Porcine reproductive and respiratory syndrome virus
<220> FEATURE:
<221> NAME/KEY: MISC_FEATURE
<222> LOCATION: (4)..(4)
<223> OTHER INFORMATION: X stands for any amino acid.
<220> FEATURE:
<221> NAME/KEY: MISC_FEATURE
<222> LOCATION: (11)..(11)
<223> OTHER INFORMATION: X stands for any amino acid.
<220> FEATURE:
<221> NAME/KEY: MISC_FEATURE
<222> LOCATION: (99)..(99)
<223> OTHER INFORMATION: X stands for any amino acid.

<400> SEQUENCE: 1

Leu Cys Gln Xaa Leu Gly Lys Ile Ile Ala Xaa Gln Asn Gln Ser Arg
1               5                   10                  15

Gly Lys Gly Pro Gly Lys Lys Asn Lys Lys Asn Pro Glu Lys Pro
            20                  25                  30

His Phe Pro Leu Ala Thr Glu Asp Val Arg His His Phe Thr Pro
        35                  40                  45

Ser Glu Arg Gln Leu Cys Leu Ser Ser Ile Gln Thr Ala Phe Asn Gln
    50                  55                  60

Gly Ala Gly Thr Cys Thr Leu Ser Asp Ser Gly Arg Ile Ser Tyr Thr
65                  70                  75                  80

Val Glu Phe Ser Leu Pro Thr His His Thr Val Arg Leu Ile Arg Val
                85                  90                  95

Thr Ala Xaa Pro Ser Ala
            100

<210> SEQ ID NO 2
<211> LENGTH: 140
<212> TYPE: PRT
<213> ORGANISM: Porcine reproductive and respiratory syndrome virus
<220> FEATURE:
<221> NAME/KEY: MISC_FEATURE
<222> LOCATION: (42)..(42)
<223> OTHER INFORMATION: X can be any amino acid.
<220> FEATURE:
<221> NAME/KEY: MISC_FEATURE
<222> LOCATION: (49)..(49)
<223> OTHER INFORMATION: X can be any amino acid.
```

```
<220> FEATURE:
<221> NAME/KEY: MISC_FEATURE
<222> LOCATION: (137)..(137)
<223> OTHER INFORMATION: X can be any amino acid.

<400> SEQUENCE: 2

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Gly Ser Leu Cys Gln Xaa Leu Gly Lys Ile Ile Ala
        35                  40                  45

Xaa Gln Asn Gln Ser Arg Gly Lys Gly Pro Gly Lys Lys Asn Lys Lys
50                  55                  60

Lys Asn Pro Glu Lys Pro His Phe Pro Leu Ala Thr Glu Asp Asp Val
65                  70                  75                  80

Arg His His Phe Thr Pro Ser Glu Arg Gln Leu Cys Leu Ser Ser Ile
                85                  90                  95

Gln Thr Ala Phe Asn Gln Gly Ala Gly Thr Cys Thr Leu Ser Asp Ser
            100                 105                 110

Gly Arg Ile Ser Tyr Thr Val Glu Phe Ser Leu Pro Thr His His Thr
        115                 120                 125

Val Arg Leu Ile Arg Val Thr Ala Xaa Pro Ser Ala
    130                 135                 140

<210> SEQ ID NO 3
<211> LENGTH: 123
<212> TYPE: PRT
<213> ORGANISM: Porcine reproductive and respiratory syndrome virus

<400> SEQUENCE: 3

Met Pro Asn Asn Asn Gly Lys Gln Gln Lys Lys Lys Gly Asp Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Pro Pro Ser Ala
        115                 120

<210> SEQ ID NO 4
<211> LENGTH: 533
<212> TYPE: PRT
<213> ORGANISM: Porcine reproductive and respiratory syndrome virus

<400> SEQUENCE: 4

Met Glu Gln Arg Ile Thr Leu Lys Glu Ala Trp Asp Arg Ser Gly Ala
1               5                   10                  15

Trp Leu Leu Pro Val Ser Leu Val Lys Arg Lys Thr Thr Leu Ala Pro
            20                  25                  30
```

```
Asn Thr Gln Thr Ala Ser Pro Arg Ala Leu Ala Asp Ser Leu Met Gln
         35                  40                  45

Leu Ala Arg Gln Val Ser Arg Leu Asn Arg Leu Ala Ala His Pro Pro
 50                  55                  60

Phe Ala Ser Trp Arg Asn Ser Glu Glu Ala Arg Thr Asp Arg Pro Ser
 65                  70                  75                  80

Gln Gln Leu Arg Ser Leu Asn Gly Glu Trp Arg Phe Ala Trp Phe Pro
                 85                  90                  95

Ala Pro Glu Ala Val Pro Glu Ser Trp Leu Glu Cys Asp Leu Pro Glu
            100                 105                 110

Ala Asp Thr Val Val Val Pro Ser Asn Trp Gln Met His Gly Tyr Asp
            115                 120                 125

Ala Pro Ile Tyr Thr Asn Val Thr Tyr Pro Ile Thr Val Asn Pro Pro
            130                 135                 140

Phe Val Pro Thr Glu Asn Pro Thr Gly Cys Tyr Ser Leu Thr Phe Asn
145                 150                 155                 160

Val Asp Glu Ser Trp Leu Gln Glu Gly Gln Thr Arg Ile Ile Phe Asp
                165                 170                 175

Gly Val Asn Ser Ala Phe His Leu Trp Cys Asn Gly Arg Trp Val Gly
                180                 185                 190

Tyr Gly Gln Asp Ser Arg Leu Pro Ser Glu Phe Asp Leu Ser Ala Phe
            195                 200                 205

Leu Arg Ala Gly Glu Asn Arg Leu Ala Val Met Val Leu Arg Trp Ser
210                 215                 220

Asp Gly Ser Tyr Leu Glu Asp Gln Asp Met Trp Arg Met Ser Gly Ile
225                 230                 235                 240

Phe Arg Asp Val Ser Leu Leu His Lys Pro Thr Thr Gln Ile Ser Asp
                245                 250                 255

Phe His Val Ala Thr Arg Phe Asn Asp Asp Phe Ser Arg Ala Val Leu
                260                 265                 270

Glu Ala Glu Val Gln Met Cys Gly Glu Leu Arg Asp Tyr Leu Arg Val
            275                 280                 285

Thr Val Ser Leu Trp Gln Gly Glu Thr Gln Val Ala Ser Gly Thr Ala
290                 295                 300

Pro Phe Gly Gly Glu Ile Ile Asp Glu Arg Gly Gly Tyr Ala Asp Arg
305                 310                 315                 320

Val Thr Leu Arg Leu Asn Val Glu Asn Pro Lys Leu Trp Ser Ala Glu
                325                 330                 335

Ile Pro Asn Leu Tyr Arg Ala Val Val Glu Leu His Thr Ala Asp Gly
            340                 345                 350

Thr Leu Ile Glu Ala Glu Ala Cys Asp Val Gly Phe Arg Glu Val Arg
            355                 360                 365

Ile Glu Asn Gly Leu Leu Leu Leu Asn Gly Lys Pro Leu Leu Ile Arg
            370                 375                 380

Gly Val Asn Arg His Glu His His Pro Leu His Gly Gln Val Met Asp
385                 390                 395                 400

Glu Gln Thr Met Val Gln Asp Gly Asp Pro Met Pro Asn Asn Asn Gly
                405                 410                 415

Lys Gln Gln Lys Lys Lys Gly Asp Gly Gln Pro Val Asn Gln Leu
            420                 425                 430

Cys Gln Met Leu Gly Lys Ile Ile Ala Gln Gln Asn Gln Ser Arg Gly
            435                 440                 445
```

Lys Gly Pro Gly Lys Lys Asn Lys Lys Asn Pro Glu Lys Pro His
            450                 455                 460

Phe Pro Leu Ala Thr Glu Asp Val Arg His His Phe Thr Pro Ser
465                 470                 475                 480

Glu Arg Gln Leu Cys Leu Ser Ser Ile Gln Thr Ala Phe Asn Gln Gly
                485                 490                 495

Ala Gly Thr Cys Thr Leu Ser Asp Ser Gly Arg Ile Ser Tyr Thr Val
                500                 505                 510

Glu Phe Ser Leu Pro Thr His His Thr Val Arg Leu Ile Arg Val Thr
            515                 520                 525

Ala Pro Pro Ser Ala
       530

<210> SEQ ID NO 5
<211> LENGTH: 161
<212> TYPE: PRT
<213> ORGANISM: Artificial Sequence
<220> FEATURE:
<223> OTHER INFORMATION: Part of U.S. PRRSV serotype ORF7 with a 37
      amino acid fusion tag is attached to amino terminus

<400> SEQUENCE: 5

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Gly Ser Leu Pro Asn Asn Asn Gly Lys Gln Gln Lys
        35                  40                  45

Lys Lys Lys Gly Asp Gly Gln Pro Val Asn Gln Leu Cys Gln Met Leu
50                  55                  60

Gly Lys Ile Ile Ala Gln Gln Asn Gln Ser Arg Gly Lys Gly Pro Gly
65                  70                  75                  80

Lys Lys Asn Lys Lys Asn Pro Glu Lys Pro His Phe Pro Leu Ala
                85                  90                  95

Thr Glu Asp Asp Val Arg His His Phe Thr Pro Ser Glu Arg Gln Leu
            100                 105                 110

Cys Leu Ser Ser Ile Gln Thr Ala Phe Asn Gln Gly Ala Gly Thr Cys
        115                 120                 125

Thr Leu Ser Asp Ser Gly Arg Ile Ser Tyr Thr Val Glu Phe Ser Leu
130                 135                 140

Pro Thr His His Thr Val Arg Leu Ile Arg Val Thr Ala Pro Pro Ser
145                 150                 155                 160

Ala

<210> SEQ ID NO 6
<211> LENGTH: 140
<212> TYPE: PRT
<213> ORGANISM: Artificial Sequence
<220> FEATURE:
<223> OTHER INFORMATION: Fusion protein comprising part of U.S. PRRSV
      serotype ORF7; amino acid number 25 - methionine is converted to
      isoleucine; a 37 amino acid fusion tag is attached to amino
      terminus of protein.

<400> SEQUENCE: 6

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Gly Ser Leu Cys Gln Ile Leu Gly Lys Ile Ile Ala
            35                  40                  45

Gln Gln Asn Gln Ser Arg Gly Lys Gly Pro Gly Lys Lys Asn Lys Lys
 50                  55                  60

Lys Asn Pro Glu Lys Pro His Phe Pro Leu Ala Thr Glu Asp Asp Val
 65                  70                  75                  80

Arg His His Phe Thr Pro Ser Glu Arg Gln Leu Cys Leu Ser Ser Ile
                85                  90                  95

Gln Thr Ala Phe Asn Gln Gly Ala Gly Thr Cys Thr Leu Ser Asp Ser
                100                 105                 110

Gly Arg Ile Ser Tyr Thr Val Glu Phe Ser Leu Pro Thr His His Thr
            115                 120                 125

Val Arg Leu Ile Arg Val Thr Ala Pro Pro Ser Ala
    130                 135                 140

<210> SEQ ID NO 7
<211> LENGTH: 161
<212> TYPE: PRT
<213> ORGANISM: Artificial Sequence
<220> FEATURE:
<223> OTHER INFORMATION: Fusion protein containing part of U.S. PRSSV
      ORF7; a 37 amino acid fusion tag is present on the amino terminus
      of the protein; an additional 30 amino acid tag encoded by the
      expression vector is attached to the carboxy terminus.

<400> SEQUENCE: 7

Met Arg Gly Ser His His His His His His Gly Met Ala Ser Met Thr
 1               5                  10                  15

Gly Gly Gln Gln Met Gly Arg Asp Leu Tyr Asp Asp Asp Asp Lys Asp
             20                  25                  30

His Pro Phe Thr Gly Ser Leu Pro Asn Asn Gly Lys Gln Gln Lys
            35                  40                  45

Lys Lys Lys Gly Asp Gly Gln Pro Val Asn Gln Leu Cys Gln Met Leu
 50                  55                  60

Gly Lys Ile Ile Ala Gln Gln Asn Gln Ser Arg Gly Lys Gly Pro Gly
 65                  70                  75                  80

Lys Lys Asn Lys Lys Lys Asn Pro Glu Lys Pro His Phe Pro Leu Ala
                85                  90                  95

Thr Glu Asp Asp Val Arg His His Phe Thr Pro Ser Glu Arg Gln Leu
                100                 105                 110

Cys Leu Ser Ser Ile Gln Thr Ala Phe Asn Gln Gly Ala Gly Thr Cys
            115                 120                 125

Thr Leu Ser Leu Glu Ser Leu Glu Lys Gly Glu Leu Asn Asp Pro Ala
            130                 135                 140

Ala Asn Lys Ala Arg Lys Glu Ala Glu Leu Ala Ala Ala Thr Ala Glu
145                 150                 155                 160

Gln

<210> SEQ ID NO 8
<211> LENGTH: 123
<212> TYPE: PRT
<213> ORGANISM: Porcine reproductive and respiratory syndrome virus

<400> SEQUENCE: 8

Met Pro Asn Asn Asn Gly Lys Gln Thr Glu Glu Lys Lys Gly Asp Gly
 1               5                  10                  15

Gln Pro Val Asn Gln Leu Cys Gln Met Leu Gly Lys Ile Ile Ala Gln

```
                   20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 9
<211> LENGTH: 123
<212> TYPE: PRT
<213> ORGANISM: Porcine reproductive and respiratory syndrome virus

<400> SEQUENCE: 9

Met Pro Asn Asn Thr Gly Lys Gln Gln Lys Arg Lys Lys Gly Asp Gly
1               5                   10                  15

Gln Pro Val Asn Gln Leu Cys Gln Met Leu Gly Lys Ile Ile Ala His
                20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Pro Pro Ser Ala
        115                 120

<210> SEQ ID NO 10
<211> LENGTH: 123
<212> TYPE: PRT
<213> ORGANISM: Porcine reproductive and respiratory syndrome virus

<400> SEQUENCE: 10

Met Pro Asn Asn Asn Gly Lys Gln Gln Lys Lys Lys Gly Asp Gly
1               5                   10                  15

Gln Pro Val Asn Gln Leu Cys Gln Met Leu Gly Lys Ile Ile Ala Gln
                20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
```

```
                    100                 105                 110

Arg Leu Ile Arg Val Thr Ala Ser Pro Ser Ala
        115                 120

<210> SEQ ID NO 11
<211> LENGTH: 123
<212> TYPE: PRT
<213> ORGANISM: Porcine reproductive and respiratory syndrome virus
<220> FEATURE:
<221> NAME/KEY: MISC_FEATURE
<222> LOCATION: (5)..(5)
<223> OTHER INFORMATION: X stands for any amino acid.
<220> FEATURE:
<221> NAME/KEY: MISC_FEATURE
<222> LOCATION: (9)..(9)
<223> OTHER INFORMATION: X stands for any amino acid.
<220> FEATURE:
<221> NAME/KEY: MISC_FEATURE
<222> LOCATION: (10)..(10)
<223> OTHER INFORMATION: X stands for any amino acid.
<220> FEATURE:
<221> NAME/KEY: MISC_FEATURE
<222> LOCATION: (32)..(32)
<223> OTHER INFORMATION: X stands for any amino acid.
<220> FEATURE:
<221> NAME/KEY: MISC_FEATURE
<222> LOCATION: (120)..(120)
<223> OTHER INFORMATION: X stands for any amino acid.

<400> SEQUENCE: 11

Met Pro Asn Asn Xaa Gly Lys Gln Xaa Xaa Glu Lys Lys Gly Asp Gly
1               5                   10                  15

Gln Pro Val Asn Gln Leu Cys Gln Met Leu Gly Lys Ile Ile Ala Xaa
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Xaa Pro Ser Ala
        115                 120

<210> SEQ ID NO 12
<211> LENGTH: 102
<212> TYPE: PRT
<213> ORGANISM: Porcine reproductive and respiratory syndrome virus
<220> FEATURE:
<221> NAME/KEY: MISC_FEATURE
<222> LOCATION: (7)..(7)
<223> OTHER INFORMATION: X stands for any amino acid.

<400> SEQUENCE: 12

Cys Gln Leu Leu Gly Ala Xaa Ile Lys Ser Gln Arg Gln Gln Pro Arg
1               5                   10                  15

Gly Gly Gln Ala Lys Lys Lys Lys Pro Glu Lys Pro His Phe Pro Leu
            20                  25                  30

Ala Ala Glu Asp Asp Ile Arg His His Leu Thr Gln Thr Glu Arg Ser
        35                  40                  45

Leu Cys Leu Gln Ser Ile Gln Thr Ala Phe Asn Gln Gly Ala Gly Thr
```

-continued

```
                    50                  55                  60
Ala Ser Leu Ser Ser Ser Gly Glu Val Ser Phe Gln Val Glu Phe Met
 65                  70                  75                  80

Leu Pro Val Ala His Thr Val Arg Leu Ile Arg Val Thr Ser Thr Ser
                     85                  90                  95

Ala Ser Gln Gly Ala Ser
                100

<210> SEQ ID NO 13
<211> LENGTH: 140
<212> TYPE: PRT
<213> ORGANISM: Artificial Sequence
<220> FEATURE:
<223> OTHER INFORMATION: His-tagged 5' truncated PRRSV Lelystad ORF7
      polypeptide
<220> FEATURE:
<221> NAME/KEY: MISC_FEATURE
<222> LOCATION: (45)..(45)
<223> OTHER INFORMATION: X stands for any amino acid

<400> SEQUENCE: 13

Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
                20                  25                  30

His Pro Phe Thr Gly Ser Cys Gln Leu Leu Gly Ala Xaa Ile Lys Ser
             35                  40                  45

Gln Arg Gln Gln Pro Arg Gly Gly Gln Ala Lys Lys Lys Pro Glu
     50                  55                  60

Lys Pro His Phe Pro Leu Ala Ala Glu Asp Asp Ile Arg His His Leu
 65                  70                  75                  80

Thr Gln Thr Glu Arg Ser Leu Cys Leu Gln Ser Ile Gln Thr Ala Phe
                 85                  90                  95

Asn Gln Gly Ala Gly Thr Ala Ser Leu Ser Ser Ser Gly Glu Val Ser
            100                 105                 110

Phe Gln Val Glu Phe Met Leu Pro Val Ala His Thr Val Arg Leu Ile
        115                 120                 125

Arg Val Thr Ser Thr Ser Ala Ser Gln Gly Ala Ser
    130                 135                 140

<210> SEQ ID NO 14
<211> LENGTH: 551
<212> TYPE: PRT
<213> ORGANISM: Artificial Sequence
<220> FEATURE:
<223> OTHER INFORMATION: beta gal-ORF7 Lelystad expressed by pEX4 vector

<400> SEQUENCE: 14

Met Glu Gln Arg Ile Thr Leu Lys Glu Ala Trp Asp Arg Ser Gly Ala
 1               5                  10                  15

Trp Leu Leu Pro Val Ser Leu Val Lys Arg Lys Thr Thr Leu Ala Pro
                20                  25                  30

Asn Thr Gln Thr Ala Ser Pro Arg Ala Leu Ala Asp Ser Leu Met Gln
             35                  40                  45

Leu Ala Arg Gln Val Ser Arg Leu Asn Arg Leu Ala Ala His Pro Pro
     50                  55                  60

Phe Ala Ser Trp Arg Asn Ser Glu Glu Ala Arg Thr Asp Arg Pro Ser
 65                  70                  75                  80

Gln Gln Leu Arg Ser Leu Asn Gly Glu Trp Arg Phe Ala Trp Phe Pro
```

```
                     85                  90                  95
Ala Pro Glu Ala Val Pro Glu Ser Trp Leu Glu Cys Asp Leu Pro Glu
            100                 105                 110
Ala Asp Thr Val Val Val Pro Ser Asn Trp Gln Met His Gly Tyr Asp
            115                 120                 125
Ala Pro Ile Tyr Thr Asn Val Thr Tyr Pro Ile Thr Val Asn Pro Pro
            130                 135                 140
Phe Val Pro Thr Glu Asn Pro Thr Gly Cys Tyr Ser Leu Thr Phe Asn
145                 150                 155                 160
Val Asp Glu Ser Trp Leu Gln Glu Gly Gln Thr Arg Ile Ile Phe Asp
            165                 170                 175
Gly Val Asn Ser Ala Phe His Leu Trp Cys Asn Gly Arg Trp Val Gly
            180                 185                 190
Tyr Gly Gln Asp Ser Arg Leu Pro Ser Glu Phe Asp Leu Ser Ala Phe
            195                 200                 205
Leu Arg Ala Gly Glu Asn Arg Leu Ala Val Met Val Leu Arg Trp Ser
            210                 215                 220
Asp Gly Ser Tyr Leu Glu Asp Gln Asp Met Trp Arg Met Ser Gly Ile
225                 230                 235                 240
Phe Arg Asp Val Ser Leu Leu His Lys Pro Thr Thr Gln Ile Ser Asp
            245                 250                 255
Phe His Val Ala Thr Arg Phe Asn Asp Asp Phe Ser Arg Ala Val Leu
            260                 265                 270
Glu Ala Glu Val Gln Met Cys Gly Glu Leu Arg Asp Tyr Leu Arg Val
            275                 280                 285
Thr Val Ser Leu Trp Gln Gly Glu Thr Gln Val Ala Ser Gly Thr Ala
            290                 295                 300
Pro Phe Gly Gly Glu Ile Ile Asp Glu Arg Gly Gly Tyr Ala Asp Arg
305                 310                 315                 320
Val Thr Leu Arg Leu Asn Val Glu Asn Pro Lys Leu Trp Ser Ala Glu
            325                 330                 335
Ile Pro Asn Leu Tyr Arg Ala Val Val Glu Leu His Thr Ala Asp Gly
            340                 345                 350
Thr Leu Ile Glu Ala Glu Ala Cys Asp Val Gly Phe Arg Glu Val Arg
            355                 360                 365
Ile Glu Asn Gly Leu Leu Leu Asn Gly Lys Pro Leu Leu Ile Arg
            370                 375                 380
Gly Val Asn Arg His Glu His His Pro Leu His Gly Gln Val Met Asp
385                 390                 395                 400
Glu Gln Thr Met Val Gln Asp Gly Asp Pro Lys Gly Phe Glu Phe Glu
            405                 410                 415
Leu Gly Thr Leu Ala Gly Lys Asn Gln Ser Gln Lys Lys Lys Ser
            420                 425                 430
Thr Ala Pro Met Gly Asn Gly Gln Pro Val Asn Gln Leu Cys Gln Leu
            435                 440                 445
Leu Gly Ala Met Ile Lys Ser Gln Arg Gln Pro Arg Gly Gly Gln
            450                 455                 460
Ala Lys Lys Lys Lys Pro Glu Lys Pro His Phe Pro Leu Ala Ala Glu
465                 470                 475                 480
Asp Asp Ile Arg His His Leu Thr Gln Thr Glu Arg Ser Leu Cys Leu
            485                 490                 495
Gln Ser Ile Gln Thr Ala Phe Asn Gln Gly Ala Gly Thr Ala Ser Leu
            500                 505                 510
```

-continued

Ser Ser Ser Gly Lys Val Ser Phe Gln Val Glu Phe Met Leu Pro Val
        515                 520                 525

Ala His Thr Val Arg Leu Ile Arg Val Thr Thr Ser Ala Ser Gln
        530                 535                 540

Gly Ala Arg Asp Pro Leu Glu
545                 550

<210> SEQ ID NO 15
<211> LENGTH: 165
<212> TYPE: PRT
<213> ORGANISM: Artificial Sequence
<220> FEATURE:
<223> OTHER INFORMATION: His-orf7 Lelystad PRRSV expressed from the
      pET200 vector

<400> SEQUENCE: 15

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Gly Leu Ala Gly Lys Asn Gln Ser Gln Lys Lys Lys
        35                  40                  45

Lys Ser Thr Ala Pro Met Gly Asn Gly Gln Pro Val Asn Gln Leu Cys
    50                  55                  60

Gln Leu Leu Gly Ala Met Ile Lys Ser Gln Arg Gln Gln Pro Arg Gly
65                  70                  75                  80

Gly Gln Ala Lys Lys Lys Lys Pro Glu Lys Pro His Phe Pro Leu Ala
                85                  90                  95

Ala Glu Asp Asp Ile Arg His His Leu Thr Gln Thr Glu Arg Ser Leu
            100                 105                 110

Cys Leu Gln Ser Ile Gln Thr Ala Phe Asn Gln Gly Ala Gly Thr Ala
        115                 120                 125

Ser Leu Ser Ser Ser Gly Lys Val Ser Phe Gln Val Glu Phe Met Leu
    130                 135                 140

Pro Val Ala His Thr Val Arg Leu Ile Arg Val Thr Thr Ser Ala
145                 150                 155                 160

Ser Gln Gly Ala Ser
            165

<210> SEQ ID NO 16
<211> LENGTH: 140
<212> TYPE: PRT
<213> ORGANISM: Artificial Sequence
<220> FEATURE:
<223> OTHER INFORMATION: His-5'Trucated ORF7 Lelystad PRRSV expressed
      from the pET200 vector

<400> SEQUENCE: 16

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Gly Ser Cys Gln Leu Leu Gly Ala Ile Ile Lys Ser
        35                  40                  45

Gln Arg Gln Gln Pro Arg Gly Gly Gln Ala Lys Lys Lys Lys Pro Glu
    50                  55                  60

Lys Pro His Phe Pro Leu Ala Ala Glu Asp Asp Ile Arg His His Leu
65                  70                  75                  80

```
Thr Gln Thr Glu Arg Ser Leu Cys Leu Gln Ser Ile Gln Thr Ala Phe
                85                  90                  95

Asn Gln Gly Ala Gly Thr Ala Ser Leu Ser Ser Ser Gly Glu Val Ser
            100                 105                 110

Phe Gln Val Glu Phe Met Leu Pro Val Ala His Thr Val Arg Leu Ile
        115                 120                 125

Arg Val Thr Ser Thr Ser Ala Ser Gln Gly Ala Ser
            130                 135                 140

<210> SEQ ID NO 17
<211> LENGTH: 127
<212> TYPE: PRT
<213> ORGANISM: Artificial Sequence
<220> FEATURE:
<223> OTHER INFORMATION: His-3' truncated ORF7 Lelystad expressed from
      the pET200 vector

<400> SEQUENCE: 17

Met Gly Ser His His His His His Gly Met Ala Ser Met Thr Gly
1               5                   10                  15

Gly Gln Gln Met Gly Arg Asp Asp Asp Lys Asp His Pro Phe Thr
            20                  25                  30

Gly Leu Ala Gly Lys Asn Gln Ser Gln Lys Lys Lys Ser Thr Ala
        35                  40                  45

Pro Met Gly Asn Gly Gln Pro Val Asn Gln Leu Cys Gln Leu Leu Gly
50                  55                  60

Ala Met Ile Lys Ser Gln Arg Gln Pro Arg Gly Gly Gln Ala Lys
65                  70                  75                  80

Lys Lys Lys Pro Glu Lys Pro His Phe Pro Leu Ala Ala Glu Asp Asp
                85                  90                  95

Ile Arg His His Leu Thr Gln Thr Glu Arg Ser Leu Cys Leu Gln Ser
            100                 105                 110

Ile Gln Thr Ala Phe Asn Gln Gly Ala Gly Thr Ala Ser Leu Ser
        115                 120                 125

<210> SEQ ID NO 18
<211> LENGTH: 102
<212> TYPE: PRT
<213> ORGANISM: Porcine reproductive and respiratory syndrome virus
<220> FEATURE:
<221> NAME/KEY: MISC_FEATURE
<222> LOCATION: (7)..(7)
<223> OTHER INFORMATION: X stands for any amino acid

<400> SEQUENCE: 18

Cys Gln Leu Leu Gly Ala Xaa Ile Lys Ser Gln Arg Gln Gln Pro Arg
1               5                   10                  15

Gly Gly Gln Ala Lys Lys Lys Lys Pro Glu Lys Pro His Phe Pro Leu
            20                  25                  30

Ala Ala Glu Asp Asp Ile Arg His His Leu Thr Gln Thr Glu Arg Ser
        35                  40                  45

Leu Cys Leu Gln Ser Ile Gln Thr Ala Phe Asn Gln Gly Ala Gly Thr
    50                  55                  60

Ala Ser Leu Ser Ser Ser Gly Glu Val Ser Phe Gln Val Glu Phe Met
65                  70                  75                  80
```

-continued

```
Leu Pro Val Ala His Thr Val Arg Leu Ile Arg Val Thr Ser Thr Ser
                85                  90                  95

Ala Ser Gln Gly Ala Ser
            100
```

US 7,572,445 B2

PEPTIDES FOR DETECTION OF ANTIBODY TO PORCINE REPRODUCTIVE RESPIRATORY SYNDROME VIRUS

PRIORITY

This application claims the benefit of U.S. Appl. No. 60/656,348, filed Feb. 25, 2005, which is incorporated herein by reference in its entirety.

FIELD OF THE INVENTION

The invention relates to methods and compositions for the detection and quantification of porcine reproductive respiratory syndrome virus (PRRSV) antibodies and antibody fragments using PRRSV polypeptides.

BACKGROUND OF THE INVENTION

Porcine reproductive and respiratory syndrome virus (PRRSV) is an Arterivirus (RNA enveloped virus) that causes porcine reproductive and respiratory syndrome (PRRS). The virus can cause major reproductive problems in adult pigs resulting in abortion. In growing pigs the symptoms include increased mortality, decreased appetite, fever, respiratory problems, pneumonia, increased secondary bacterial infections, and atrophic rhinitis. In neonatal pigs the virus can cause respiratory distress, a failure to thrive, and increased secondary bacterial infections. The virus is spread primarily by pig to pig. The virus can also be spread through infected feces, urine and milk to piglets without colostral antibodies. Additionally, transmission through needles, insects, and air is possible.

Methods of detection of PRRSV are needed in the art. PRRS antibody detection kits are commercially available such as, for example, the HerdChek® PRRS Antibody 2XR Test Kit (IDEXX Labs, Inc., Westbrook, Me.).

SUMMARY OF THE INVENTION

One embodiment of the invention provides a composition of matter comprising a purified polypeptide consisting essentially of SEQ ID NO: 1 or SEQ ID NO: 12. The purified polypeptide can further comprise one or more amino acids at either terminus that are not contiguously associated with a PRRSV ORF7 in nature. The purified polypeptide can be in a multimeric form. The composition can further comprise a carrier. The purified polypeptide can be linked to an indicator reagent, an amino acid spacer, an amino acid linker, a signal sequence, a stop transfer sequence, a transmembrane domain, a protein purification ligand, or a combination thereof. The purified polypeptide can consist essentially of SEQ ID NO: 2 or SEQ ID NO: 13 and one or more polypeptides not contiguously associated with SEQ ID NO: 1, SEQ ID NO: 2, SEQ ID NO:18, or SEQ ID NO: 13 in nature. The one or more polypeptides not contiguously associated with SEQ ID NO: 1, SEQ ID NO: 2, SEQ ID NO: 18, or SEQ ID NO: 13 in nature can be non-PRRSV polypeptides.

Another embodiment of the invention provides a purified fusion polypeptide comprising a polypeptide consisting essentially of SEQ ID NO: 1 or SEQ ID NO: 18 and one or more polypeptides not contiguously associated with SEQ ID NO: 1 or SEQ ID NO: 18 in nature. The one or more polypeptides not contiguously associated with SEQ ID NO: 1 or SEQ ID NO: 18 in nature can be a non-PRRSV polypeptide. SEQ ID NO: 1 or SEQ ID NO: 18 can be in multimeric form. The purified fusion polypeptide can comprise an indicator reagent, an amino acid spacer, an amino acid linker, a signal sequence, a stop transfer sequence, a transmembrane domain, a protein purification ligand or a combination thereof. The purified polypeptide can consist essentially of SEQ ID NO: 2 or SEQ ID NO: 13.

Yet another embodiment of the invention provides a purified polynucleotide encoding the purified polypeptides and purified fusion polypeptides of the invention.

Still another embodiment of the invention provides a method of detecting antibodies that specifically bind reproductive respiratory syndrome virus (PRRSV) or a PRRSV polypeptide. The method comprises contacting a purified polypeptide consisting essentially of SEQ ID NO: 1, SEQ ID NO: 2, SEQ ID NO: 18, or SEQ ID NO: 13 or a combination thereof, with a test sample suspected of comprising antibodies specific for PRRSV, under conditions that allow polypeptide/antibody complexes to form and detecting polypeptide/antibody complexes. The detection of polypeptide/antibody complexes is an indication that antibodies specific for PRRSV are present in the test sample, and the absence of polypeptide/antibody complexes is an indication that antibodies specific for PRSSV are not present in the test sample. The method can further comprise contacting the polypeptide/antibody complexes with an indicator reagent comprising prior to their detection. The antibodies can be fragments of antibodies. The amount of antibody in the test sample can be determined. The polypeptide can be attached to a substrate. The polypeptide can be in a multimeric form. The polypeptide can be a fusion protein comprising SEQ ID NO: 1, SEQ ID NO: 2, SEQ ID NO: 18, or SEQ ID NO: 13 or a combination thereof and one or more polypeptides not contiguously associated with SEQ ID NO: 1, SEQ ID NO:2, SEQ ID NO: 18, or SEQ ID NO: 13 in nature. The one or more polypeptides not contiguously associated with SEQ ID NO: 1, SEQ ID NO: 2, SEQ ID NO: 18, or SEQ ID NO: 13 in nature can be non-PRRSV polypeptides. The test sample can comprise a biological sample obtained from a mammal. The method can comprise an assay selected from the group of assays consisting of a reversible flow chromatographic binding assay, an enzyme linked immunosorbent assay, a radioimmunoassay, a hemagglutination assay, a western blot assay, a fluorescence polarization immunoassay, and an indirect immunofluorescence assay.

Even another embodiment of the invention provides a method of detecting a PRRSV infection in a mammal. The method comprises obtaining a biological sample from a mammal suspected of having a PRRSV infection; contacting a purified polypeptide consisting essentially of SEQ ID NO: 1, SEQ ID NO: 2, SEQ ID NO: 18, or SEQ ID NO: 13 or a combination thereof, with the biological sample under conditions that allow polypeptide/antibody complexes to form; and detecting polypeptide/antibody complexes. The detection of polypeptide/antibody complexes is an indication that the mammal has a PRSSV infection and the absence of polypeptide/antibody complexes is an indication that the mammal does not have a PRRSV infection. The method can further comprise contacting the polypeptide/antibody complexes with an indicator reagent that generates a measurable signal prior to the detection. The polypeptide can be a fusion protein consisting essentially of SEQ ID NO: 1, SEQ ID NO: 2, SEQ ID NO: 18, or SEQ ID NO: 13 or a combination thereof and one or more polypeptides not contiguously associated with SEQ ID NO: 1, SEQ ID NO: 2, SEQ ID NO: 18, or SEQ ID NO: 13 in nature.

Another embodiment of the invention provides an antibody that specifically binds to at least one epitope of a PRRSV polypeptide, wherein said polypeptide is SEQ ID NO: 1, SEQ ID NO:2, SEQ ID NO: 18, or SEQ ID NO: 13. The antibody can be a monoclonal antibody, polyclonal antibody or antibody fragment.

Yet another embodiment of the invention provides a method of detecting a PRRSV polypeptide or PRRSV in a sample. The method comprises contacting one or more antibodies that specifically bind to at least one epitope of an PRRSV polypeptide, wherein said polypeptide comprises SEQ ID NO: 1, SEQ ID NO: 2, or SEQ ID NO: 18, or SEQ ID NO: 13 with the sample under conditions that allow polypeptide/antibody complexes to form; and detecting polypeptide/antibody complexes. The detection of polypeptide/antibody complexes is an indication that PRSSV or a PRSSV polypeptide is present in the sample and the absence of polypeptide/antibody complexes is an indication that PRSSV or a PRRSV polypeptide is not present in the sample. The one or more antibodies are monoclonal antibodies, polyclonal antibodies, or antibody fragments. The sample can be serum, whole blood, sputum, milk, meat juice, lung lavage fluid, lung tissue, tonsil tissue, or lymph node tissue.

Another embodiment of the invention provides a method of decreasing the incidence of false positives in a diagnostic assay that detects PRRSV antibodies specific for PRRSV ORF 7. The method comprises using a PRRSV ORF 7 polypeptide comprising about 19 to about 28 N-terminal amino acid deletions as an antibody capture antigen in the diagnostic assay. The PRRSV ORF7 polypeptide can be SEQ ID NO: 1 or SEQ ID NO: 18. The polypeptide can further comprise one or more amino acids at either terminus that are not contiguously associated with a PRRSV ORF7 in nature.

The invention therefore provides methods and compositions that can be used to detect PRRSV antibodies and antibody fragments using polypeptides with sensitivity and specificity.

DETAILED DESCRIPTION OF THE INVENTION

PRRSV Polypeptides

A polypeptide is a polymer of three or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

Purified polypeptides of the invention can either be full-length polypeptides or fragments of polypeptides.

The sequences of three US ORF 7 strains of PRRSV: VR-2332 (Bold) (U.S. Pat. No. 5,998,601) (SEQ ID NO: 8); ISU-12 (Underlined)(SEQ ID NO: 9); and US-A (Italics) (SEQ ID NO: 10) are compared in Table 1.

TABLE 1

| M<br>Met<br>1 | P<br>Pro | N<br>Asn | N<br>Asn | N<br>Asn<br>T<br>Thr<br>5 | G<br>Gly | K<br>Lys | Q<br>Gln | T<br>Thr<br>Q<br>Gln<br>Q<br>Gln | E<br>Glu<br>K<br>Lys<br>K<br>Lys<br>10 | E<br>Glu<br>R<br>Arg<br>K<br>Lys | K<br>Lys | K<br>Lys | G<br>Gly | D<br>Asp<br>15 | G<br>Gly |
|---|---|---|---|---|---|---|---|---|---|---|---|---|---|---|---|
| Q<br>Gln | P<br>Pro | V<br>Val | N<br>Asn<br>20 | Q<br>Gln | L<br>Leu | C<br>Cys | Q<br>Gln | M<br>Met<br>25 | L<br>Leu | G<br>Gly | K<br>Lys | I<br>Ile | I<br>Ile<br>30 | A<br>Ala | Q<br>Gln<br>H<br>His |
| Q<br>Gln | N<br>Asn | Q<br>Gln<br>35 | S<br>Ser | R<br>Arg | G<br>Gly | K<br>Lys | G<br>Gly<br>40 | P<br>Pro | G<br>Gly | K<br>Lys | K<br>Lys | N<br>Asn<br>45 | K<br>Lys | K<br>Lys | K<br>Lys |
| N<br>Asn | P<br>Pro<br>50 | E<br>Glu | K<br>Lys | P<br>Pro | H<br>His | F<br>Phe<br>55 | P<br>Pro | L<br>Leu | A<br>Ala | T<br>Thr | E<br>Glu<br>60 | D<br>Asp | D<br>Asp | V<br>Val | R<br>Arg |
| H<br>His<br>65 | H<br>His | F<br>Phe | T<br>Thr | P<br>Pro | S<br>Ser<br>70 | E<br>Glu | R<br>Arg | Q<br>Gln | L<br>Leu | C<br>Cys<br>75 | L<br>Leu | S<br>Ser | S<br>Ser | I<br>Ile | Q<br>Gln<br>80 |
| T<br>Thr | A<br>Ala | F<br>Phe | N<br>Asn | Q<br>Gln<br>85 | G<br>Gly | A<br>Ala | G<br>Gly | T<br>Thr | C<br>Cys<br>90 | T<br>Thr | L<br>Leu | S<br>Ser | D<br>Asp | S<br>Ser<br>95 | G<br>Gly |
| R<br>Arg | I<br>Ile | S<br>Ser | Y<br>Tyr<br>100 | T<br>Thr | V<br>Val | E<br>Glu | F<br>Phe | S<br>Ser<br>105 | L<br>Leu | P<br>Pro | T<br>Thr | H<br>His | H<br>His<br>110 | T<br>Thr | V<br>Val |
| R<br>Arg | L<br>Leu | I<br>Ile<br>115 | R<br>Arg | V<br>Val | T<br>Thr | A<br>Ala | S<br>Ser<br>P<br>Pro<br>120 | P<br>Pro | S<br>Ser | A<br>Ala | | | | | |

The relative identity of the three strains is shown in Table 2.

TABLE 2

|        | VR-2332 | ISU-12 | US-A |
|--------|---------|--------|------|
| VR-2332 | 100    | 95.9   | 96.7 |
| ISU-12  | 95.9   | 100    | 96.7 |
| US-A    | 96.7   | 96.7   | 100  |

The consensus sequence is shown in SEQ ID NO: 11:

| MPNNXGKQXX | EKKGDGQPVN | QLCQMLGKII | AXQNQSRGKG |     | 40  |
|------------|------------|------------|------------|-----|-----|
| PGKKNKKKNP | EKPHFPLATE | DDVRHHFTPS | ERQLCLSSIQ |     | 80  |
| TAFNQGAGTC | TLSDSGRISY | TVEFSLPTHH | TVRLIRVTAX | PSA | 123 |

The X at position 5 can be N or T. In another embodiment the X at position 5 can be any amino acid. The X at position 9 can be Q or T. In another embodiment the X at position 9 can be any amino acid. The X at position 10 can be E or K. In another embodiment the X at position 10 can be any amino acid. The X at position 11 can be E, R or K. In another embodiment the X at position 11 can be any amino acid. The X at position 32 can be Q or H. In another embodiment the X at position 32 can be any amino acid. The X at position 120 can be S or P. In another embodiment the X at position 120 can be any amino acid.

In one embodiment of the invention a polypeptide comprises a portion of a U.S. serotype PRRSV ORF7:

(SEQ ID NO: 1)
LCQXLGKIIAXQNQSRGKGPGKKNKKKNPEKPHFPLATEDDVRHHFTP

SERQLCLSSIQTAFNQGAGTCTLSDSGRISYTVEFSLPTHHTVRLIRVTA

XPSA.

The X at position 11 can be any amino acid. In other embodiments the X at position 11 can be Q or H. The X at position 99 can be any amino acid. In other embodiments, the X at position 99 can be P or S. The X at position 4 can be any amino acid.

In another embodiment of the invention, a polypeptide comprises a portion of a U.S. serotype PRRSV ORF7 and a histidine tag:

MRGSHHHHHHGMASMTGGQQMGRDLYDDDDKD (SEQ ID NO:2)
HPFTGSLCQXLGKIIAXQNQSRGKGPGKKNKKKNPEK
PHFPLATEDDVRHHFTPSERQLCLSSIQTAFNQGAGT
CTLSDSGRISYTVEFSLPTHHTVRLIRVTAXPSA.

The X at position 42 stands for any amino acid. In certain embodiments the X at position 42 can be M or I. The X at position 49 stands for any amino acid. In certain embodiments the X at position 49 stands for Q or H. The X at position 137 stands for any amino acid. In certain embodiments the X at position 137 stands for P or S.

Another embodiment provides an N terminal truncated PRRSV Lelystad ORF7 polypeptide.

(SEQ ID NO: 12)
CQLLGAXIKSQRQQPRGGQAKKKKPEKPHFPLAAEDDIRHHLTQTERSLCL

QSIQTAFNQGAGTASLSSSGEVSFQVEFMLPVAHTVRLIRVTSTSASQGA

S.

The X at position 7 stands for any amino acid. In certain embodiments, the X at position 7 can be either M or I. Another embodiment is CQLLGAXIKSQRQQPRGGQAKKKKPE-KPHFP LAAEDDIRHHLTQTERSLCLQSIQTAFN-QGAGTASLSSSGEVSFQVEFMLPVAHTVRLIR VTST-SASQGAS (SEQ ID NO: 18). The X at position 7 can be any amino acid. In preferred embodiments the X at position 7 is M or I.

Another embodiment provides a His-tagged N-truncated PRRSV Lelystad ORF7 polypeptide:

(SEQ ID NO:13)
MRGSHHHUHHGMASMTGGQQMGRDLYDDDDKDHPFTGSCQLLGAXIKSQ
RQQPRGGQAKKKKPEKPHFPLAAEDDIRHHLTQTERSLCLQSIQTAFNQ
GAGTASLSSSGEVSFQVEFMLPVAHTVRLIRVTSTSASQGAS.

The X at position 45 stands for any amino acid. In certain embodiments, the X at position 45 can be either M or I.

In one embodiment of the invention SEQ ID NO: 1 SEQ ID NO: 2, SEQ ID NO: 12, and/or SEQ ID NO: 13 are more soluble than a polypeptide comprising a full length PRRSV ORF7. Additionally, the polypeptides of the invention specifically bind to antibodies specific for PRRSV. Therefore, the basic and novel characteristics of polypeptides of the invention is that they can be more soluble than a full length PRRSV ORF7, they have greater specificity in PRRSV detection assays than full length PRRSV ORF7, and they specifically bind to anti-PRRSV antibodies.

One embodiment of the invention provides less than full length PRRSV ORF7 polypeptides. In particular the PRRSV ORF7 polypeptides have N-terminal truncations. That is, the polypeptides have about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43 amino acids removed from the N-terminus. In a preferred embodiment of the invention a PRRSV ORF7 polypeptide has about 15, 16, 17, 18, 19, 20, 21, 22, 23, 24, 25, 26, 27, 28, 29, 30, 31, or 32 amino acids removed from the N-terminus. In other embodiments, a PRRSV ORF 7 polypeptide has about 16 to about 31 amino acids removed from the N-terminus; about 17 to about 30 amino acids removed from the N-terminus; about 18 to about 29 amino acids removed from the N-terminus; about 19 to about 28 amino acids removed from the N-terminus; about 20 to about 27 amino acids removed from the N-terminus; or about 21 to about 26 amino acids removed from the N-terminus. If present, the M residue that occurs in US PRRSV ORF 7 at about position 25 and the at about position 33 of Lelystad PRRSV can be replaced with another amino acid. See, e.g., SEQ ID NO: 1 and SEQ ID NO: 18.

Fragments of polypeptides of the invention can comprise about 5, 10, 15, 20, 30, 40, 50, 60, 70, 80, or more amino acids of polypeptides of the invention. Variant polypeptides are at least about 80, or about 90, 96, 98, or 99% identical to the polypeptide sequences shown in SEQ ID NO:1, SEQ ID NO: 2, SEQ ID NO: 12, or SEQ ID NO: 13 and are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g., has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide. Variant polypeptides of the invention can comprise about 1, 2, 3, 4, 5, or 6 conservative amino acid substitutions.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature. Additionally, a polypeptide can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. An amino acid spacer is a sequence of amino acids that are not usually contiguously associated with a polypeptide of the invention in nature. An amino acid spacer can comprise about 1, 5, 10, 20, 100, 1,000 or more amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and staphylococcal protein A, or combinations thereof. More than one polypeptide of the invention can be present in a fusion protein. Fragments of polypeptides of the invention can be present in a fusion protein of the invention. A fusion protein of the invention can comprise one or more of SEQ ID NO: 1, SEQ ID NO: 2, SEQ ID NO:12, SEQ ID NO: 13, fragments thereof, or combinations thereof.

Polypeptides of the invention can be in a multimeric form. That is, a polypeptide can comprise one or more copies of SEQ ID NO: 1, SEQ ID NO: 2, SEQ ID NO: 12, and/or SEQ ID NO:13. A multimeric polypeptide can be a multiple antigen peptide (MAP). See e.g., Tam, J. Immunol. Methods, 196:17-32 (1996).

Polypeptides of the invention can comprise an antigen that is recognized by an antibody reactive against PRRSV. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, *CABIOS* 4:181-186 (1988). For example, a polypeptide of the invention can be isolated and screened. A series of short peptides, which together span an entire polypeptide sequence, can be prepared by proteolytic cleavage. By starting with, for example, 20-mer polypeptide fragments, each fragment can be tested for the presence of epitopes recognized in an ELISA. For example, in an ELISA assay a PRRSV polypeptide, such as a 20-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 20-mer to map the epitope of interest.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from PRRSV cultures.

PRRSV Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. The polynucleotides of the invention encode the polypeptides described above. In one embodiment of the invention the polynucleotides encode a polypeptide shown in SEQ ID NO: 1, SEQ ID NO: 2, SEQ ID NO: 12, SEQ ID NO: 13, or combinations thereof. Polynucleotides of the invention can comprise other nucleotide sequences, such as sequences coding for linkers, spacers, signal sequences, TMR stop transfer sequences, transmembrane domains, or ligands useful in protein purification such as glutathione-S-transferase, histidine tag, and staphylococcal protein A.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of PRRSV polynucleotides that encode biologically functional PRRSV polypeptides also are PRRSV polynucleotides.

Polynucleotides of the invention can be isolated from nucleic acid sequences present in, for example, a biological sample, such as saliva, blood, milk, meat juice, serum, lung lavage fluid, sputum, lung, tonsil, lymph node or other tissue sample, urine, feces, cerebrospinal fluid, amniotic fluid, or wound exudates. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Polynucleotides of the invention can be used, for example, as probes or primers, for example PCR primers, to detect the presence of PRRSV polynucleotides in a sample, such as a biological sample. The ability of such probes and primers to specifically hybridize to PRRSV polynucleotide sequences will enable them to be of use in detecting the presence of complementary sequences in a given sample. Polynucleotide probes and primers of the invention can hybridize to complementary sequences in a sample such as a biological sample, including saliva, blood, serum, milk, meat juice, lung lavage fluid, sputum, lung, tonsil, lymph node or other tissue sample, urine, feces, cerebrospinal fluid, amniotic fluid, or wound exudate. Polynucleotides from the sample can be, for example, subjected to gel electrophoresis or other size separation techniques or can be immobilized without size separation. The polynucleotide probes or primers can be labeled. Suitable labels, and methods for labeling probes and primers are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging from about 20° C. to about 55° C. The presence of a hybridized complex comprising the probe or primer and a complementary polynucleotide from the test sample indicates the presence of PRRSV or a PRRSV polynucleotide sequence in the sample.

Antibodies

Antibodies of the invention are antibody molecules that specifically and stably bind to a PRRSV polypeptide of the invention or fragments thereof. An antibody of the invention can be a polyclonal antibody, a monoclonal antibody, a single chain antibody (scFv), or a fragment of an antibody. Fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'—SH, F(ab')$_2$ and F$_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that a first antigen, e.g., a polypeptide, recognizes and binds to an antibody of the invention with greater affinity than to other, non-specific molecules. A non-specific molecule is an antigen that shares no common epitope with the first antigen. For example, an antibody raised against an antigen (e.g., a polypeptide) to which it binds more efficiently than to a non-specific antigen can be described as specifically binding to the antigen. In a preferred embodiment, an antibody or antigen-binding portion thereof specifically binds to a polypeptide consisting of SEQ ID NO: 1, 2, 12, or 13 (or other sequence of the invention) when it binds with a binding affinity $K_a$ of $10^7$ l/mol or more. Specific binding can be tested using, for example, an enzyme-linked immunosorbant assay (ELISA), a radioimmunoassay (RIA), or a western blot assay using methodology well known in the art.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing PRRSV-specific antibodies can be identified using RIA or ELISA and isolated by cloning in semi-solid agar or by limiting dilution. Clones producing PRRSV-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J Immunolog. Meth.* 74:307, 1984. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); Presta, *Curr. Op. Struct. Biol.* 2:593 (1992)), or human antibodies. Human antibodies can be made by, for example, direct immortilization, phage display, transgenic mice, or a Trimera methodology, see e.g., Reisener et al., *Trends Biotechnol.* 16:242-246 (1998).

Antibodies that specifically bind PRRSV antigens (e.g., PRRSV polypeptides), are particularly useful for detecting the presence of PRRSV or PRRSV antigens in a sample, such as a saliva, blood, serum, milk, meat juice, lung lavage fluid, sputum, lung, tonsil, lymph node or other tissue sample, urine, feces, cerebrospinal fluid, amniotic fluid, or wound exudate sample from a PRRSV-infected animal such as a pig. An immunoassay for PRRSV or a PRRSV antigen can utilize one antibody or several antibodies. An immunoassay for PRRSV or an PRRSV antigen can use, for example, a monoclonal antibody directed towards an PRRSV epitope, a combination of monoclonal antibodies directed towards epitopes of one PRRSV polypeptide, monoclonal antibodies directed towards epitopes of different PRRSV polypeptides, polyclonal antibodies directed towards the same PRRSV antigen, polyclonal antibodies directed towards different PRRSV antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or fragments thereof can be bound to a support and used to detect the presence of PRRSV or a PRRSV antigen. Supports include, for example, glass, polystyrene, polypropylene, polyethylene, dextran, nylon, amylases, natural and modified celluloses, polyacrylamides, agaroses and magletite.

Antibodies of the invention can further be used to isolate PRRSV or PRRSV antigens by immunoaffinity columns. The antibodies can be affixed to a solid support by, for example, adsorbtion or by covalent linkage so that the antibodies retain their immunoselective activity. Optionally, spacer groups can be included so that the antigen binding site of the antibody remains accessible. The immobilized antibodies can then be used to bind PRRSV or PRRSV antigens from a sample, such as a biological sample including saliva, blood, serum, milk, meat juice, lung lavage fluid, sputum, lung, tonsil, lymph node or other tissue sample, urine, feces, cerebrospinal fluid, amniotic fluid, or wound exudate. The bound PRRSV or PRRSV antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by PRRSV. By measuring the increase or decrease of PRRSV antibodies to PRRSV antigens in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Methods of Detection

The methods of the invention can be used to detect antibodies or antibody fragments specific for PRRSV in a test sample, such as a biological sample, an environmental sample, or a laboratory sample. A biological sample can include, for example, saliva, blood, serum, milk, meat juice, lung lavage fluid, sputum, lung, tonsil, lymph node or other tissue sample, urine, feces, cerebrospinal fluid, amniotic fluid, or wound exudate from an animal such as a horse, cat, dog, pig, or human. The test sample can be untreated, precipitated, fractionated, separated, diluted, concentrated, or purified before combining with a polypeptide of the invention.

The methods comprise contacting a polypeptide of the invention with a test sample under conditions that allow a polypeptide/antibody complex to form. That is, a polypeptide of the invention specifically binds to an antibody specific for PRRSV located in the sample. In this embodiment a polypeptide of the invention is acting as an antibody capture reagent. One of skill in the art is familiar with assays and conditions that are used to detect antibody/polypeptide complex binding. The formation of a complex between polypeptides and anti-PRRSV antibodies in the sample is detected.

An antibody of the invention can be used in a method of the diagnosis of PRRSV infection by obtaining a test sample from a human or animal suspected of having a PRRSV infection. The test sample is contacted with an antibody of the invention under conditions enabling the formation of an antibody-antigen complex (i.e., an immunocomplex). The amount of antibody-antigen complexes can be determined by methodology known in the art. A level that is higher than that formed in a control sample indicates a PRRSV infection. Alternatively, a polypeptide of the invention can be contacted with a test sample. PRRSV antibodies in a positive body sample will form an antigen-antibody complex under suitable conditions. The amount of antibody-antigen complexes can be determined by methods known in the art.

In one embodiment of the invention, the polypeptide/antibody complex is detected when an indicator reagent, such as an enzyme, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

Assays of the invention include, but are not limited to those based on competition, direct reaction or sandwich-type assays, including, but not limited to enzyme linked immunosorbent assay (ELISA), western blot, IFA, radioimmunoassay (RIA), hemagglutination (HA), and fluorescence polarization immunoassay (FPIA). One assay of the invention comprises a reversible flow chromatographic binding assay, for example a SNAP® assay. See U.S. Pat. No. 5,726,010.

Assays can use solid phases or substrates or can be performed by immunoprecipitation or any other methods that do not utilize solid phases. Where a solid phase or substrate is used, a polypeptide of the invention is directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). In one embodiment, a substrate is sintered, fine particles of polyethylene, commonly known as porous polyethylene, for example, 10-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

In one type of assay format, one or more polypeptides can be coated on a solid phase or substrate. A test sample suspected of containing an anti-PRRSV antibody or fragment thereof is incubated with an indicator reagent comprising a signal generating compound conjugated to an antibody or antibody fragment specific for PRRSV for a time and under conditions sufficient to form antigen/antibody complexes of either antibodies of the test sample to the polypeptides of the solid phase or the indicator reagent compound conjugated to an antibody specific for PRRSV to the polypeptides of the solid phase. The reduction in binding of the indicator reagent conjugated to an anti PRRSV antibody to the solid phase can be quantitatively measured. A measurable reduction in the signal compared to the signal generated from a confirmed negative PRRSV test sample indicates the presence of anti-PRRSV antibody in the test sample. This type of assay can quantitate the amount of anti-PRRSV antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If PRRSV antibodies are present in the test sample they will bind the polypeptide conjugated to an indicator reagent and to the polypeptide immobilized on the support. The polypeptide/antibody/indicator complex can then be detected. This type of assay can quantitate the amount of anti-PRRSV antibodies in a test sample.

In another type of assay format, one or more polypeptides of the invention are coated onto a support or substrate. The test sample is applied to the support or substrate and incubated. Unbound components from the sample are washed away by washing the solid support with a wash solution. If PRRSV antibodies are present in the test sample, they will bind to the polypeptide coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of anti-PRRSV antibodies in a test sample.

The formation of a polypeptide/antibody complex or a polypeptide/antibody/indicator complex can be detected by radiometric, colormetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzymes, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzymes include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-PRRSV antibodies in a test sample. Therefore, the methods of the invention can be used to diagnose PRRSV infection in a patient.

The methods of the invention can also indicate the amount or quantity of anti-PRRSV antibodies in a test sample. With many indicator reagents, such as enzymes, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrate specimens such as urine, in order to determine the presence and/or amount of antibody present.

The invention further comprises assay kits (e.g., articles of manufacture) for detecting anti-PRRSV antibodies or antibody fragments or PRRSV polypeptides in a sample. A kit comprises one or more polypeptides of the invention and means for determining binding of the polypeptide to anti-PRRSV antibodies or antibody fragments in the sample. A kit or article of manufacture can also comprise one or more antibodies or antibody fragments of the invention and means for determining binding of the antibodies or antibody fragments to PRRSV or PRRSV polypeptides in the sample. A kit can comprise a device containing one or more polypeptides or antibodies of the invention and instructions for use of the one or more polypeptides or antibodies for, e.g., the identification of a PRRSV infection in a mammal. The kit can also comprise packaging material comprising a label that indicates that the one or more polypeptides or antibodies of the kit can be used for the identification of PRRSV infection. Other components such as buffers, controls, and the like, known to those of ordinary skill in art, can be included in such test kits. The polypeptides, antibodies, assays, and kits of the invention are useful, for example, in the diagnosis of individual cases of PRRSV infection in a patient, as well as epidemiological studies of PRRSV outbreaks. Polypeptides and assays of the invention can be combined with other polypeptides or assays to detect the presence of PRRSV along with other organisms.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above. All references cited in this disclosure are incorporated herein by reference.

EXAMPLES

Example 1

PEXUSorf7 was expressed and purified as described previously (EMBO J. 1984, 3: 1429-1434). Recombinant full length U.S.ORF7, N-terminal deletion derivative U.S.ORF7 and Carboxy-terminal deletion derivative U.S.ORF7 proteins were expressed using a Studier pET expression system using methods described by the manufacturer (EMD Biosciences, Ind., Madison, Wis. 53719). The nucleic acids encoding the proteins described below were cloned into the pET200 expression system using methods described by the manufacturer. The recombinant proteins were expressed with a histidine tag at the amino terminus that is encoded by the vector allowing for rapid affinity purification. The proteins were expressed and purified from the *E. coli* strain BL21(star) using methods described by the manufacturer (EMD Biosciences). Crude lysates of *E. coli* were separated using SDS-PAGE gels, the separated proteins were blotted to nitrocellulose, and the nitrocellulose blot blocked using standard techniques known to those of ordinary skill in the art. See e.g., Sambrook and Russell, "Molecular Cloning: A Laboratory Manual" ($3_{rd}$ Edition, Cold Spring Harbor Laboratory Press, Cold Spring Harbor, N.Y., 2001). Presence of swine antibodies were detected with goat anti-swine IgG HRP conjugate (Jackson ImmunoResearch Laboratories Inc., West Grove, Pa., 19390) using standard techniques known to those of ordinary skill in the art.

The sequence of PRSSV (U.S. serotype) open reading frame 7 (ORF7) is 123 amino acids in length and is shown below: Porcine Reproductive Respiratory Syndrome Virus, U.S. Serotype

MPNNNGKQQKKKKGDGQPVNQLCQMLGKIIAQQNQSR    (SEQ ID NO:3)

GKGPGKKNKKKNPEKPHFPLATEDDVRHHFTPSERQL

CLSSIQTAFNQGAGTCTLSDSGRISYTVEFSLPTHHT

VRLIRVTAPPSA

The amino acid sequence of PEXUSorf7 is shown in SEQ ID NO: 4. The amino acids from PRRS ORF7, U.S. serotype are in BOLD and UNDERLINED. All 123 amino acids of ORF7 are present.

MEQRITLKEAWDRSGAWLLPVSLVKRKTTLAPNTQTASP    SEQ ID NO:4

RALADSLMQLARQVSRLNRLAAHPPFASWRNSEEARTDR

PSQQLRSLNGEWRFAWFPAPEAVPESWLECDLPEADTVV

VPSNWQMHGYDAPIYTNVTYPITVNPPFVPTENPTGCYS

LTFNVDESWLQEGQTRIIFDGVNSAFHLWCNGRWVGYGQ

DSRLPSEFDLSAFLRAGENRLAVMVLRWSDGSYLEDQDM

WRMSGIFRDVSLLHKPTTQISDFHVATRFNDDFSRAVLE

AEVQMCGELRDYLRVTVSLWQGETQVASGTAPFGGEIID

ERGGYADRVTLRLNVENPKLWSAEIPNLYRAVVELHTAD

GTLIEAEACDVGFREVRIENGLLLLNGKPLLIRGVNRHE

HHPLHGQVMDEQTMVQDGDPMPNNNGKQQKKKKGDGQPV

NQLCQMLGKIIAQQNQSRGKGPGKKNKKKNPEKPHFPLA

TEDDVRHHFTPSERQLCLSSIQTAFNQGAGTCTLSDSGR

ISYTVEFSLPTHHTVRLIRVTAPPSA.

Amino acids 2 through 123 of U.S. serotype ORF7 are present and are BOLD and UNDERLINED in SEQ ID NO: 5. This recombinant protein was expressed using pET200 expression vector from Novagen. A 37 amino acid fusion tag is attached to amino terminus of protein.

MRGSHHHHHHGMASMTGGQQMGRDLYDDDDKDHPFTGSL    SEQ ID NO:5

PNNNGKQQKKKKGDGQPVNQLCQMLGKIIAQQNQSRGKG

PGKKNKKKNPEKPHFPLATEDDVRHHFTPSERQLCLSSI

QTAFNQGAGTCTLSDSGRISYTVEFSLPTHHTVRLIRVT

APPSA.

21 amino acids were deleted from the ORF7 amino terminus. Amino acids 22 through 123 are present, U.S. serotype ORF7 amino acids are in BOLD and UNDERLINED in SEQ ID NO:6. Recombinant protein expressed using pET200 expression vector from Novagen. Amino acid number 25 (of the full length PRRS protein)—methionine (M)—is converted to isoleucine (I)—to remove aberrant translational start site. This protein carries the same 37 amino acid fusion tag attached to amino terminus of protein.

MRGSHHHHHHGMASMTGGQQMGRDLYDDDDKDHPFTGSL    SEQ ID NO:6

CQILGKIIAQQNQSRGKGPGKKNKKKNPEKPHFPLATED

DVRHHFTPSERQLCLSSIQTAFNQGAGTCTLSDSGRISY

TVEFSLPTHHTVRLIRVTAPPSA.

30 amino acids from the carboxy terminus of U.S. ORF7 were deleted. Amino acids 2 through 93 of U.S. ORF7 are present and are BOLD and UNDERLINED in SEQ ID NO: 7. The recombinant protein was expressed using pET200 expression vector from Novagen. This protein carries the same 37 amino acid fusion tag attached to amino terminus of protein. This protein has an additional 30 amino acid tag attached to the carboxy terminus that is encoded for by the vector that is NOT from the PRRS virus.

MRGSHHHHHHGMASMTGGQQMGRDLYDDDDKDHPFTGSL    SEQ ID NO:7

PNNNGKQQKKKKGDGQPVNQLCQMLGKIIAQQNQSRGKG

PGKKNKKKNPEKPHFPLATEDDVRHHFTPSERQLCLSSI

QTAFNQGAGTCTLSLESLEKGELNDPAANKARKEAELAA

ATAEQ

Example 2

Reactivity in Western blot:

This data demonstrates the C-Terminal deletion derivative of U.S.ORF7 (SEQ ID NO: 7) does not react with positive swine sera in a Western blot, where as the full length U.S.ORF7 and N-Terminal (a.k.a. amino-terminal) deletion derivative of U.S. ORF 7 (SEQ ID NO: 6) both react with positive swine sera.

TABLE 3

|  | Positive Swine Sera | Negative Swine Sera |
|---|---|---|
| PEXUSorf7 (SEQ ID NO: 4) | Positive | Negative |
| Full length U.S.ORF7 (SEQ ID NO: 5) | Positive | Negative |
| N-Terminal derivative U.S.ORF7 (SEQ ID NO: 6) | Positive | Negative |
| C-Terminal derivative U.S.ORF7 (SEQ ID NO: 7) | Negative | Negative |

Example 3

Reactivity in ELISA

Recombinant protein was expressed using a Studier pET expression system using methods described by the manufacturer (EMD Biosciences, Ind., Madison, Wis. 53719). The genes encoding the proteins described above were cloned into the pET200 expression system using methods described by the manufacturer. The recombinant proteins are expressed with a histidine tag at the amino terminus that is encoded by the vector that allows rapid affinity purification. The protein was expressed and purified from the *E. coli* strain BL21 (star) using methods described by the manufacturer (EMD Biosciences).

Immulon 1 plates were coated overnight at 4° C. with purified recombinant protein at 1 ug/ml in carbonate buffer, pH9.5. Plates were emptied by "flicking" and patting dry.

Plates were blocked overnight using 2.5% BSA in PBS. Plates were "flicked" and patted dry and over-coated with 2.5% sucrose in 10 mM Tris buffer (pH7.5). After flicking and patting dry, plates were vacuum dried for 4 hours and stored with desiccant.

Samples were tested on these ELISA plates using commercially available reagents and methods from the "Porcine Reproductive and Respiratory Syndrome Virus Antibody Test Kit" (IDEXX Laboratories Inc., Westbrook Me., catalog number 06-04404-00). The results demonstrated that the N-Terminal deletion derivative of U.S.ORF7 protein (SEQ ID NO: 6) reacts in a similar manner as the full-length protein in an ELISA assay (SEQ ID No:5).

Example 4

The following Lelystad PRRSV ORF 7 polypeptides were made using techniques well known in the art. Sequences from a Lelystad ORF7 protein are BOLD and UNDERLINED. Other amino acids are fusion partners/tags added to these recombinant proteins.

Sequence of beta gal-ORF7 Lelystad expressed by pEX4 vector:

MEQRITLKEAWDRSGAWLLPVSLVKRKTTLAPNTQT (SEQ ID NO:14)
ASPRALADSLMQLARQVSRLNRLAAHPPFASWRNSE
EARTDRPSQQLRSLNGEWRFAWFPAPEAVPESWLEC
DLPEADTVVVPSNWQMHGYDAPIYTNVTYPITVNPP
FVPTENPTGCYSLTFNVDESWLQEGQTRIIFDGVNS
AFHLWCNGRWVGYGQDSRLPSEFDLSAFLRAGENRL
AVMVLRWSDGSYLEDQDMWRMSGIFRDVSLLHKPTT
QISDFHVATRFNDDFSRAVLEAEVQMCGELRDYLRV
TVSLWQGETQVASGTAPFGGEIIDERGGYADRVTLR
LNVENPKLWSAEIPNLYRAVVELHTADGTLIEAEAC
DVGFREVRIENGLLLLNGKPLLIRGVNRHEHHPLHQ
GQVMDEQTMVQDGDPKGFEFELGTLAGKNQSQKKKK
STAPMGNGQPVNQLCQLLGAMIKSQRSSPRGGQAKK
KKPEKPHFPLAAEDDIRHHLTQTERSLCLQSIQTAF
NQGAGTASLSSSGKVSFQVEFMLPVAHTVRLIRVTS
TSASQGA**RDPLE

Sequence of His-orf7 Lelystad expressed from the pET200 vector.

MRGSHHHHHHGMASMTGGQQMGRDLYDDDDKDHPFT (SEQ ID NO:15)
GLAGKNQSQKKKKSTAPMGNGQPVNQLCQLLGAMIK
SQRQQPRGGQAKKKKPEKPHFPLAAEDDIRHHLTQT
ERSLCLQSIQTAFNQGAGTASLSSSGKVSFQVEFML
PVAHTVRLIRVTSTSASQGAS

Sequence of the His-N-Terminal Truncated ORF7 Lelystad expressed from the pET200 vector. This N-Terminal deletion peptide has 26 amino acids removed from the amino terminus:

MRGSHHHHHHGMASMTGGQQMGRDLYDDDDKDHPFT (SEQ ID NO:16)
GSCQLLGAIIKSQRQQPRGGQAKKKKPEKPHFPLAA
EDDIRHHLTQTERSLCLQSIQTAFNQGAGTASLSSS
GEVSFQVEFMLPVAHTVRLIRVTSTSASQGAS

Sequence of the His Carboxy Truncated ORF7 Lelystad expressed from the pET200 vector. This C-Terminal deletion peptide has 34 amino acids removed from the carboxy terminus:

MGSHHHHHHGMASMTGGQQMGRDDDDKDHPFTGLAG (SEQ ID NO:17)
KNQSQKKKKSTAPMGNGQPVNQLCQLLGAMIKSQRQ
QPRGGQAKKKKPEKPHFPLAAEDDIRHHLTQTERSL
CLQSIQTAFNQGAGTASLS.

The reactivity of these polypeptides was tested using a Western blot. The results are shown in Table 4.

TABLE 4

| | Positive Swine Sera | Negative Swine Sera |
| --- | --- | --- |
| PEXLorf7 (SEQ 14) | Positive | Negative |
| Full length Lelystad ORF7 (SEQ 15) | Positive | Negative |
| N-Terminal Deletion derivative Lelystad ORF7 (SEQ 16) | Positive | Negative |
| C-Terminal Deletion derivative Lelystad ORF7 (SEQ 17) | Negative | Negative |

This data demonstrates the C-Terminal deletion derivative of Lelystad ORF7 does not react with positive swine sera in a Western blot, where as the full length Lelystad ORF7 and N-Terminal deletion derivative of Lelystad ORF 7 both react with positive swine sera.

Example 5

Reactivity in ELISA

Recombinant protein was expressed using a Studier pET expression system using methods described by the manufacturer (EMD Biosciences, Ind., Madison, Wis. 53719). The nucleic acids encoding the polypeptides described above were cloned into the pET200 expression system using methods described by the manufacturer. The recombinant polypeptides are expressed with a histidine tag at the amino terminus that is encoded by the vector that allows rapid affinity purification. The protein was expressed and purified from the E. coli strain BL21 (star) using methods described by the manufacturer (EMD Biosciences). Immulon 1 plates were coated overnight at 4° C. with purified recombinant protein at 1 ug/ml in carbonate buffer, pH9.5. Plates were emptied by "flicking" and patting dry. Plates were blocked overnight using 2.5% BSA in PBS. Plates were "flicked" and patted dry and over-coated with 2.5% sucrose in 10 mM Tris buffer (pH7.5). After flicking and patting dry, plates were vacuum dried for 4 hours and stored with desiccant. Samples were tested on these ELISA plates using commercially available reagents and methods from the "Porcine Reproductive and Respiratory Syndrome Virus Antibody Test Kit" (IDEXX Laboratories Inc., Westbrook Me., catalog number 06-04404-

00). This data demonstrates the N-Terminal deletion derivative of Lelystad ORF7 protein is as reactive as the full-length protein in an ELISA assay.

Example 6

Improved Specificity of Antibody Detection Using Truncated U.S. orf7 Antigen.

The N-Terminal truncated polypeptide of the US Orf7 (SEQ ID NO: 6) generated by recombinant protein expression was tested for immunoreactivity in ELISA format and compared to full length US Orf7 (SEQ ID NO: 5). Recombinant proteins of SEQ ID NOs:5 and 6 were expressed and purified as described previously (Example 3). Immulon® plates were coated with the polypeptides as described previously (Example 3). Plate coating and secondary antibody dilutions were optimized to yield approximately equivalent specific signal to that of the IDEXX HerdCheck® 2XR ELISA assay using positive control swine sera. Reactivity toward selected swine sera was assessed by ELISA (see table 7).

Screened sera samples were designated as negative for PRRSV by other methodology including IFA and PCR, yet exhibited reactivity on IDEXX HerdCheck® 2XR ELISA. This suggests the presence of non-specific signal on the 2XR plate. Serum samples with these characteristics are false positives on IDEXX HerdCheck® 2XR ELISA and are commonly referred to as "singletons" by those skilled in the art of PRRS diagnostics. Deletion of the N-terminal 26 amino acids from US Orf7 resulted in an immunoreactive antigen displaying reduced reactivity and improved specificity as compared to full length US Orf7 (79% specificity vs. 69% specificity respectively). The $OD_{650}$ value of $\leq 0.200$ was determined as the cut off value for which samples are considered negative based upon optimization to IDEXX HerdCheck® 2XR employing positive and negative control standards. Truncation of the amino-terminal portion of the U.S. orf7 antigen caused a significant reduction in the non-specific signal from swine sera.

TABLE 5

| U.S. Antigen | Full Length Positive | Full Length Negative | 69% Specificity |
|---|---|---|---|
| N Trn   Positive | 12 | 2 | |
| Negative | 8 | 44 | |
| 79% Specificity | | | |

Example 7

Improved specificity of antibody detection using truncated Lelystad orf7 antigen Full length Orf7 (SEQ ID NO: 15) from the Lelystad strain of PRRS virus, as well as the N-terminal truncated version SEQ ID NO: 16) were expressed in *E. coli* and isolated for ELISA analysis against selected swine sera as previously described (Example 5). Plate coating and secondary antibody (conjugate) dilutions were optimized to yield specific signal that was approximately equivalent to that of the IDEXX HerdCheck® 2XR ELISA assay using positive control sera. Screened sera samples were designated as negative for PRRSV by other methodology including IFA and PCR, yet exhibited reactivity on IDEXX HerdCheck® 2XR ELISA.

The N-terminal truncated Lelystad orf7 protein exhibited reduced immunoreactivity and improved specificity when compared to full-length Lelystad orf7 protein (62% specificity compared to 42% specificity respectfully). The $OD_{650}$ value of $\leq 0.200$ was determined as the cut off value for which samples are considered negative based upon optimization to IDEXX HerdCheck 2XR employing positive and negative control standards. Truncation of the N-Terminal portion of the Lelystad orf7 antigen caused a significant reduction in the non-specific signal from swine sera.

TABLE 6

| Lelystad Antigen | Full Length Positive | Full Length Negative | 42% Specificity |
|---|---|---|---|
| N Trn   Positive | 20 | 5 | |
| Negative | 18 | 23 | |
| 62% Specificity | | | |

Table 7 Reactivity of "singleton" sera samples with full length and truncated orf7 polypeptides in ELISA. $OD_{650}$ values are shown for full length (FL) and N-Terminal truncated (Trn) polypeptides. An OD>0.2 is positive (bold values).

| Sample | U.S. orf7 Antigen Trn | U.S. orf7 Antigen F.L. | Lelystad orf7 Antigen Trn | Lelystad orf7 Antigen FL |
|---|---|---|---|---|
| 40840 - 2 | 0.176 | 0.214 | 0.077 | 0.071 |
| 4057:80 - 6 | 0.195 | 0.181 | 0.237 | 0.207 |
| 42635 - 44 | 0.068 | 0.064 | 0.081 | 0.073 |
| 42628 - 8 | 0.091 | 0.473 | 0.118 | 0.124 |
| 40860 - 23 | 0.119 | 0.156 | 0.171 | 0.176 |
| 42958 - 27 | 0.083 | 0.080 | 0.125 | 0.261 |
| 42945 - 2 | 0.082 | 0.090 | 0.080 | 0.203 |
| 4057:86F - 8 | 0.102 | 0.089 | 0.338 | 0.572 |
| 4057:86F - 10 | 0.094 | 0.080 | 0.273 | 0.439 |
| 4057:86F - 1 | 0.098 | 0.086 | 0.334 | 0.560 |
| 4057:86F - 5 | 0.100 | 0.095 | 0.309 | 0.488 |
| 4057:86F - 6 | 0.108 | 0.094 | 0.313 | 0.562 |
| 4057:86F - 9 | 0.095 | 0.083 | 0.330 | 0.521 |
| 4057:86F - 3 | 0.100 | 0.083 | 0.317 | 0.515 |
| 024403 - 2 | 0.145 | 0.159 | 0.173 | 0.544 |
| 42449 - 68 | 0.039 | 0.039 | 0.041 | 0.041 |
| 4057:86F - 7 | 0.100 | 0.086 | 0.333 | 0.556 |
| 4057:86F - 4 | 0.097 | 0.083 | 0.304 | 0.509 |
| 021290 - 324 | 0.512 | 0.519 | 0.129 | 0.462 |
| 41134 - 11 | 0.117 | 0.121 | 0.272 | 0.290 |
| 019278 - 7 | 0.102 | 0.095 | 0.176 | 0.560 |
| 41423 - 13 | 0.095 | 0.087 | 0.101 | 0.086 |
| 39852 - 3 | 0.066 | 0.069 | 0.081 | 0.073 |
| 4057:80 - 1 | 0.124 | 0.115 | 0.135 | 0.305 |
| 019276 - 12 | 0.105 | 0.089 | 0.121 | 0.127 |
| 4057:80 - 2 | 0.151 | 0.243 | 0.205 | 0.177 |
| 019523 - 13 | 0.093 | 0.098 | 0.151 | 0.145 |
| 019323 - 4 | 0.084 | 0.076 | 0.109 | 0.336 |
| 42958 - 44 | 0.441 | 0.338 | 0.287 | 0.161 |
| 39470 - 31 | 0.227 | 0.192 | 0.160 | 0.205 |
| 019278 - 29 | 0.278 | 0.241 | 0.403 | 0.343 |
| 019972 - 28 | 0.522 | 0.382 | 0.437 | 0.288 |
| 41134 - 10 | 0.086 | 0.074 | 0.092 | 0.257 |
| 020570 - 17 | 0.107 | 0.094 | 1.176 | 0.635 |
| 022081 - 55 | 0.159 | 0.131 | 0.203 | 0.222 |
| 022081 - 53 | 0.208 | 0.939 | 0.243 | 0.224 |
| P-5000 - 1 | 0.141 | 0.099 | 0.191 | 0.407 |
| 4057:80 - 5 | 0.135 | 0.152 | 0.207 | 0.163 |
| P-5004 | 0.107 | 0.101 | 0.141 | 0.116 |
| 39472 - 8 | 0.593 | 0.679 | 0.080 | 0.077 |
| 39852 - 7 | 0.064 | 0.069 | 0.088 | 0.097 |
| 40860 - 24 | 0.449 | 0.607 | 0.242 | 0.171 |
| 022081 - 37 | 0.110 | 0.789 | 0.170 | 0.531 |
| 022060 - 22 | 0.104 | 0.095 | 0.154 | 0.536 |
| 4057:80 - 4 | 0.595 | 0.594 | 0.210 | 0.185 |

| | U.S. orf7 Antigen | | Lelystad orf7 Antigen | |
|---|---|---|---|---|
| Sample | Trn | F.L. | Trn | FL |
| 019278 - 44 | 0.179 | 0.140 | 0.143 | 0.125 |
| P 5003 - 3 | 0.106 | 0.514 | 0.141 | 0.112 |
| P 5003 - 1 | 0.118 | 0.592 | 0.151 | 0.116 |
| 018911 - 13 | 1.344 | 1.127 | 0.152 | 0.143 |
| P 5003 - 2 | 0.112 | 0.578 | 0.154 | 0.115 |
| 034916 - 26 | 0.077 | 0.066 | 0.140 | 0.287 |
| 021687 - 8 | 0.074 | 0.080 | 0.121 | 0.763 |
| 4057:80 - 3 | 0.248 | 0.241 | 0.282 | 0.406 |
| 41423 - 25 | 0.086 | 0.091 | 0.095 | 0.073 |
| P-5000 - 2 | 0.102 | 0.093 | 0.145 | 0.119 |
| 41932 - 8 | 0.066 | 0.071 | 0.090 | 0.754 |

| | U.S. orf7 Antigen | | Lelystad orf7 Antigen | |
|---|---|---|---|---|
| Sample | Trn | F.L. | Trn | FL |
| 019278 - 30 | 0.137 | 0.145 | 1.004 | 0.675 |
| 028676 - 58 | 0.092 | 0.084 | 0.107 | 0.131 |
| 42945 - 56 | 0.124 | 1.347 | 0.158 | 0.145 |
| 4057:80 - 7 | 1.163 | 1.217 | 0.454 | 0.674 |
| 021378 - 513 | 0.146 | 0.148 | 0.158 | 0.280 |
| 4057:80 - 8 | 0.209 | 0.196 | 0.142 | 0.185 |
| 019276 - 27 | 0.090 | 0.081 | 1.106 | 1.227 |
| 42635 - 10 | 1.502 | 1.585 | 0.155 | 0.099 |
| 018912 - 11 | 0.124 | 0.135 | 0.108 | 2.074 |
| 024177 - 3 | 0.120 | 0.104 | 0.155 | 0.346 |

What is claimed is:

1. A composition of matter comprising one or more purified polypeptides consisting of the amino acid sequence set forth in SEQ ID NO: 1 or SEQ ID NO: 18 or a composition of matter comprising one or more purified polypeptides consisting of the amino acid sequence set forth in SEQ ID NO: 1 or SEQ ID NO: 18, wherein the one or more purified polypeptides are linked to an indicator reagent, a signal sequence, a stop transfer sequence, a transmembrane domain, a protein purification ligand, or a combination thereof.

2. The composition of matter of claim 1, wherein the one or more purified polypeptides are in a multimeric form.

3. The composition of matter of claim 1, further comprising a carrier.

4. The composition of matter of claim 1, wherein one or more purified polypeptides consist of the amino acid sequence set forth in SEQ ID NO: 2 or SEQ ID NO: 13.

5. A purified fusion polypeptide comprising one or more polypeptides consisting of the amino acid sequence set forth in SEQ ID NO: 1 or SEQ ID NO: 18, and one or more polypeptides not contiguously associated with the amino acid sequence set forth in SEQ ID NO: 1 or SEQ ID NO: 18 in nature.

6. The purified fusion protein of claim 5, wherein the one or more polypeptides consisting of the amino acid sequence set forth in SEQ ID NO: 1 or SEQ ID NO: 18 are in multimeric form.

7. The purified fusion protein of claim 5, wherein the purified fusion polypeptide comprises an indicator reagent, an amino acid spacer, an amino acid linker, a signal sequence, a stop transfer sequence, a transmembrane domain, a protein purification ligand or a combination thereof.

8. The purified fusion protein of claim 5, wherein the one or more polypeptides consist of an amino acid sequence set forth in SEQ ID NO: 2 or SEQ ID NO: 13.

9. A purified polynucleotide encoding the purified polypeptide of claim 1.

10. A purified polynucleotide encoding the purified fusion polypeptide of claim 5.

11. A method of detecting antibodies that specifically bind reproductive respiratory syndrome virus (PRRSV) or a PRRSV polypeptide comprising:

(a) contacting a composition of matter comprising one or more purified polypeptides consisting of the amino acid sequence set forth in SEQ ID NO: 1, SEQ ID NO: 2, SEQ ID NO: 18, SEQ ID NO: 13, or a composition of matter comprising one or more purified polypeptides consisting of the amino acid sequence set forth in SEQ ID NO: 1, SEQ ID NO: 2, SEQ ID NO: 13 or SEQ ID NO: 18, wherein the one or more purified polypeptides are linked to an indicator reagent, a signal sequence, a stop transfer sequence, a transmembrane domain, a protein purification ligand, or a combination thereof, with a test sample suspected of comprising antibodies specific for PRRSV, under conditions that allow polypeptide/antibody complexes to form;

(b) detecting polypeptide/antibody complexes;

wherein the detection of polypeptide/antibody complexes is an indication that antibodies specific for PRRSV are present in the test sample, and wherein the absence of polypeptide/antibody complexes is an indication that antibodies specific for PRSSV are not present in the test sample.

12. The method of claim 11, further comprising contacting the complexes of (a) with an indicator reagent comprising prior to the performance of (b).

13. The method of claim 11, wherein the antibodies are fragments of antibodies.

14. The method of claim 11, wherein the amount of antibody in the test sample is determined.

15. The method of claim 11, wherein the polypeptide is attached to a substrate.

16. The method of claim 11, wherein the polypeptide is in a multimeric form.

17. The method of claim 11, wherein the test sample comprises a biological sample obtained from a mammal.

18. The method of claim 11, wherein the method comprises an assay selected from the group of assays consisting of a reversible flow chromatographic binding assay, an enzyme linked immunosorbent assay, a radioimmunoassay, a hemagglutination assay a western blot assay, a fluorescence polarization immunoassay, and an indirect immunofluorescence assay.

19. A method of detecting a PRRSV infection in a mammal comprising:

(a) obtaining a biological sample from a mammal suspected of having a PRRSV infection;

(b) contacting a composition of matter comprising one or more purified polypeptides consisting of SEQ ID NO: 1, SEQ ID NO: 2, SEQ ID NO: 18, or SEQ ID NO: 13, or a composition of matter comprising one or more purified polypeptides consisting of the amino acid sequence set forth in SEQ ID NO: 1, SEQ ID NO: 2, SEQ ID NO: 13, or SEQ ID NO: 18, wherein the one or more purified polypeptides are linked to an indicator reagent, a signal sequence, a stop transfer sequence, a transmembrane domain, a protein purification ligand, or a combination thereof, with the biological sample under conditions that allow polypeptide/antibody complexes to form;

(c) detecting polypeptide/antibody complexes;

wherein the detection of polypeptide/antibody complexes is an indication that the mammal has a PRRSV infection and wherein the absence of polypeptide/antibody complexes is an indication that the mammal does not have a PRRSV infection.

20. The method of claim 19, further comprising contacting the polypeptide/antibody complexes of (b) with an indicator reagent that generates a measurable signal prior to the performance of (c).

21. A method of decreasing the incidence of false positives in a diagnostic assay that detects PRRSV antibodies specific for PRRSV ORF 7 comprising:

using a composition of matter comprising one or more purified polypeptides consisting of SEQ ID NO: 1, SEQ ID NO: 2, SEQ ID NO: 13 or SEQ ID NO: 18 or a composition of matter comprising one or more purified polypeptides consisting of the amino acid sequence set forth in SEQ ID NO: 1, SEQ ID NO: 2, SEQ ID NO: 13, or SEQ ID NO: 18, wherein the one or more purified polypeptides are linked to an indicator reagent, a signal sequence, a stop transfer sequence, a transmembrane domain, a protein purification ligand, or a combination thereof as an antibody capture antigen in the diagnostic assay.

22. A composition of matter comprising one or more purified polypeptides consisting of the amino acid sequence set forth in SEQ ID NO: 1 or SEQ ID NO:18 and one or more amino acids at either terminus that are not contiguously associated with a PRRSV ORF7 in nature.

* * * * *

UNITED STATES PATENT AND TRADEMARK OFFICE
CERTIFICATE OF CORRECTION

PATENT NO.      : 7,572,445 B2                                    Page 1 of 1
APPLICATION NO. : 11/362599
DATED           : August 11, 2009
INVENTOR(S)     : Eugene Regis Krah, III It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 448 days.

Signed and Sealed this

Seventh Day of September, 2010

David J. Kappos
*Director of the United States Patent and Trademark Office*